US00PP20062P2

(12) United States Plant Patent
Renken

(10) Patent No.: US PP20,062 P2
(45) Date of Patent: Jun. 9, 2009

(54) ***ILEX* PLANT NAMED 'GOLDEN ROCK'**

(50) Latin Name: *Ilex crenata*
Varietal Denomination: Northern Lights

(75) Inventor: Uwe Renken, Wiesmoor (DE)

(73) Assignee: Baumschule Karl von Hammel, Wiesmoor (DE)

( * ) Notice: Subject to any disclaimer, the term of this patent is extended or adjusted under 35 U.S.C. 154(b) by 0 days.

(21) Appl. No.: 12/011,388

(22) Filed: Jan. 25, 2008

(51) Int. Cl.
*A01H 5/00* (2006.01)

(52) U.S. Cl. ..... Plt./247
(58) Field of Classification Search ..... Plt./247
See application file for complete search history.

*Primary Examiner*—Annette H Para
(74) *Attorney, Agent, or Firm*—C. A. Whealy

(57) ABSTRACT

A new and distinct cultivar of *Ilex* plant named 'Golden Rock', characterized by its broad and upright plant habit; freely branching habit; yellow green and yellow variegated foliage; and good garden performance.

3 Drawing Sheets

Botanical designation: *Ilex crenata.*
Cultivar denomination: 'Northern Lights'.

BACKGROUND OF THE INVENTION

The present Invention relates to a new and distinct cultivar of *Ilex,* botanically known as *Ilex crenata,* and hereinafter referred to by the name 'Golden Rock'.

The new *Ilex* is a naturally-occurring branch mutation of the *Ilex crenata* cultivar Golden Gem, not patented. The new *Ilex* was discovered and selected by the Inventor from with a population of plants of the cultivar Golden Gem in a controlled environment in Wiesmoor, Germany during the summer of 2000.

Asexual reproduction of the new *Ilex* by softwood cuttings taken in a controlled environment in Wiesmoor, Germany since the summer of 2000 has shown that the unique features of this new *Ilex* are stable and reproduced true to type in successive generations.

SUMMARY OF THE INVENTION

The new *Ilex* has not been observed under all possible environmental conditions. The phenotype may vary somewhat with variations in environment such as temperature and/or light intensity without, however, any variance in genotype. The following traits have been repeatedly observed and are determined to be the unique characteristics of 'Golden Rock'. These characteristics in combination distinguish 'Golden Rock' as a new and distinct cultivar of *Ilex:*

1. Broad and upright plant habit.
2. Freely branching habit.
3. Yellow green and yellow variegated foliage.
4. Good garden performance.

Plants of the new *Ilex* differ from plants of the parent, the cultivar Golden Gem, primarily in foliage color as plants of the cultivar Golden Gem have greenish yellow-colored foliage. In addition, plants of the new *Ilex* are not as spreading as plants of the cultivar Golden Gem.

Plants of the new *Ilex* can be compared to the plants of the *Ilex crenata* cultivar Carolina Upright, not patented. In side-by-side comparisons conducted in Wiesmoor, Germany, plants of the new *Ilex* differed from plants of the cultivar Carolina Upright primarily in foliage color as plants of the cultivar Carolina Upright have green-colored foliage.

BRIEF DESCRIPTION OF THE PHOTOGRAPHS

The accompanying colored photographs illustrate the overall appearance of the new *Ilex.* These photographs show the colors as true as it is reasonably possible to obtain in colored reproductions of this type. Colors in the photographs may differ slightly from the color values cited in the detailed botanical description, which accurately describe the colors of the new *Ilex.*

The photograph on the first sheet comprises a side perspective view of typical plants of 'Golden Rock' grown in an outdoor nursery.

The photograph on the second sheet is a close-up view of a typical plant of 'Golden Rock'.

The photograph on the third sheet is a close-up view of a typical lateral branch of 'Golden Rock'.

DETAILED BOTANICAL DESCRIPTION

The aforementioned photographs and following observations and measurements describe plants grown in Stroe, The Netherlands in 7.5-liter containers, in an outdoor nursery during the summer and under commercial production conditions. During the production of the plants, day temperatures ranged from 15° C. to 32° C. and night temperatures ranged from 7° C. to 17° C. Plants used for the photographs and description were about six years old. In the following description, color references are made to The Royal Horticultural Society Colour Chart, 2001 Edition, except where general terms of ordinary dictionary significance are used.

Botanical classification: *Ilex crenata* 'Golden Rock'.
Parentage: Naturally-occurring branch mutation of the *Ilex crenata* cultivar Golden Gem, not patented.
Propagation:
*Type.*—By softwood cuttings.
*Time to initiate roots, summer.*—About 45 days at temperatures of 25° C.

*Time to produce a rooted young plant, summer.*—About four months at temperatures of 25° C.

*Root description.*—Medium in thickness, moderately fleshy; greyish brown in color.

*Rooting habit.*—Moderate branching; moderately dense.

Plant description:

*Plant form and growth habit.*—Perennial evergreen shrub; broad and upright plant habit; inverted triangle. Moderately vigorous growth habit.

*Branching habit.*—Freely branching habit; one primary lateral branches and about 42 secondary lateral branches developing per plant.

*Plant height.*—About 62 cm.

*Plant diameter, area of spread.*—About 59 cm.

*Lateral branch description.*—Length: About 41.4 cm. Diameter: About 3 mm. Internode length: About 6 mm. Strength: Very strong. Texture, young stems: Moderately pubescent. Texture, mature stems: Smooth, glabrous. Color, young stems: N144A. Color, mature stems: Slightly darker than between 195A and 197A.

*Foliage description.*—Arrangement: Alternate, simple. Length: About 1.9 cm. Width: About 9 mm. Shape: Obovate. Apex: Broadly acute. Base: Broadly attenuate. Margin: Serrate, about eight "teeth" per cm. Venation pattern: Pinnate. Texture, upper and lower surfaces: Smooth, glabrous; thick and leathery. Color: Developing foliage, upper surface: Between 144A and N144C. Developing foliage, lower surface: 144C. Fully expanded foliage, upper surface: 143A, irregularly splashed with 12A or completely yellow, 12A; venation, 144C to 144D. Fully expanded foliage, lower surface: 144B, irregularly splashed with 11B or completely yellow, 11B; venation, 144C to 144D. Petiole: Length: About 2 mm. Diameter: About 0.75 mm. Texture, upper and lower surfaces: Smooth, glabrous. Color, upper and lower surfaces: Between 144C and 1B.

Flower description: A description of the flowers is not available to date as flower development has not been observed on plants of the new *Ilex*.

Garden performance: Plants of the new *Ilex* have been observed to have good garden performance and to be tolerant to rain and wind. Plants of the new *Ilex* are hardy to USDA Zone 6 and tolerate high temperatures up to 35° C.

Disease/pest resistance: Plants have not been observed to be resistant to pathogens and pests common to *Ilex*.

It is claimed:

1. A new and distinct cultivar of *Ilex* plant named 'Golden Rock' as illustrated and described.

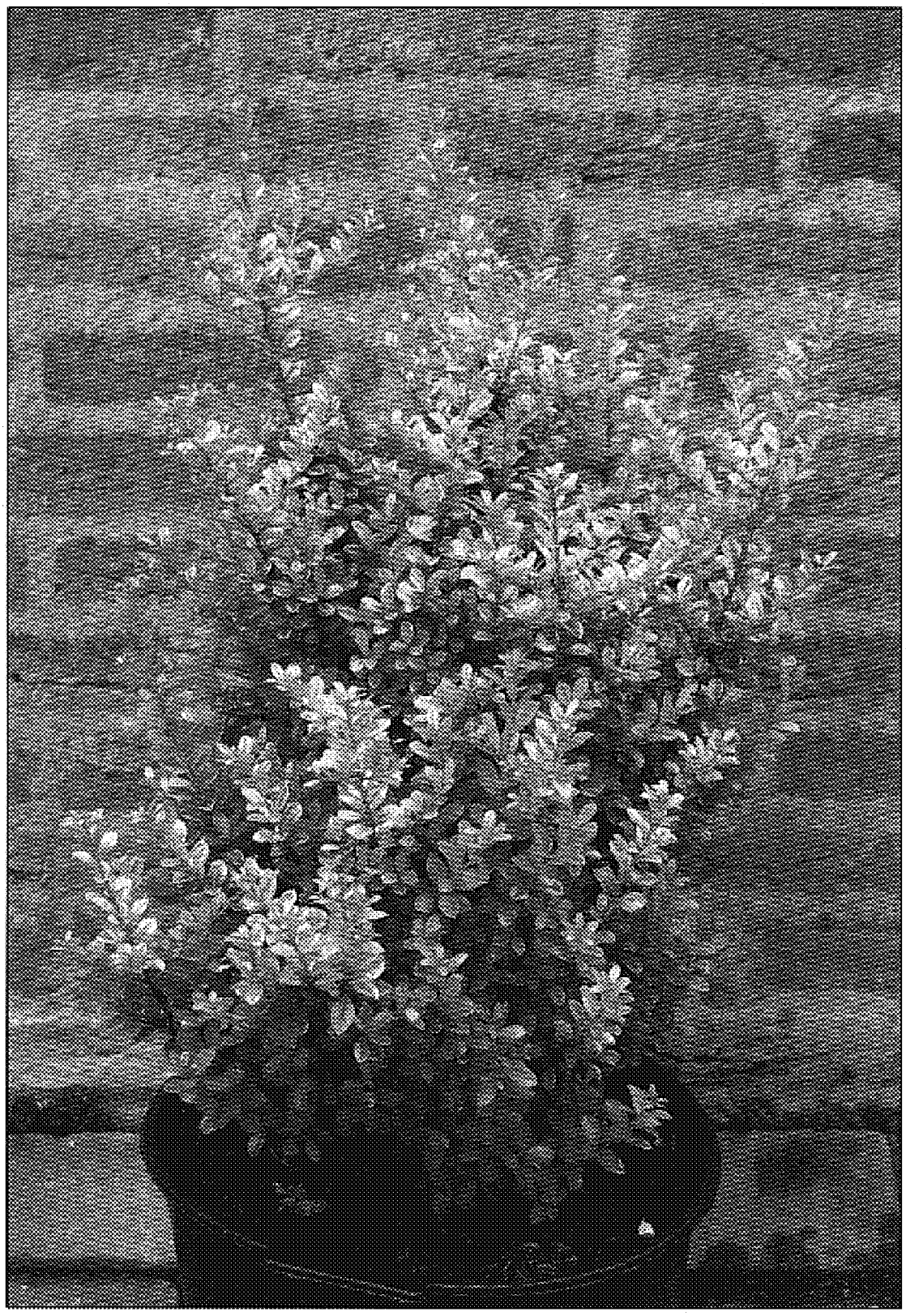

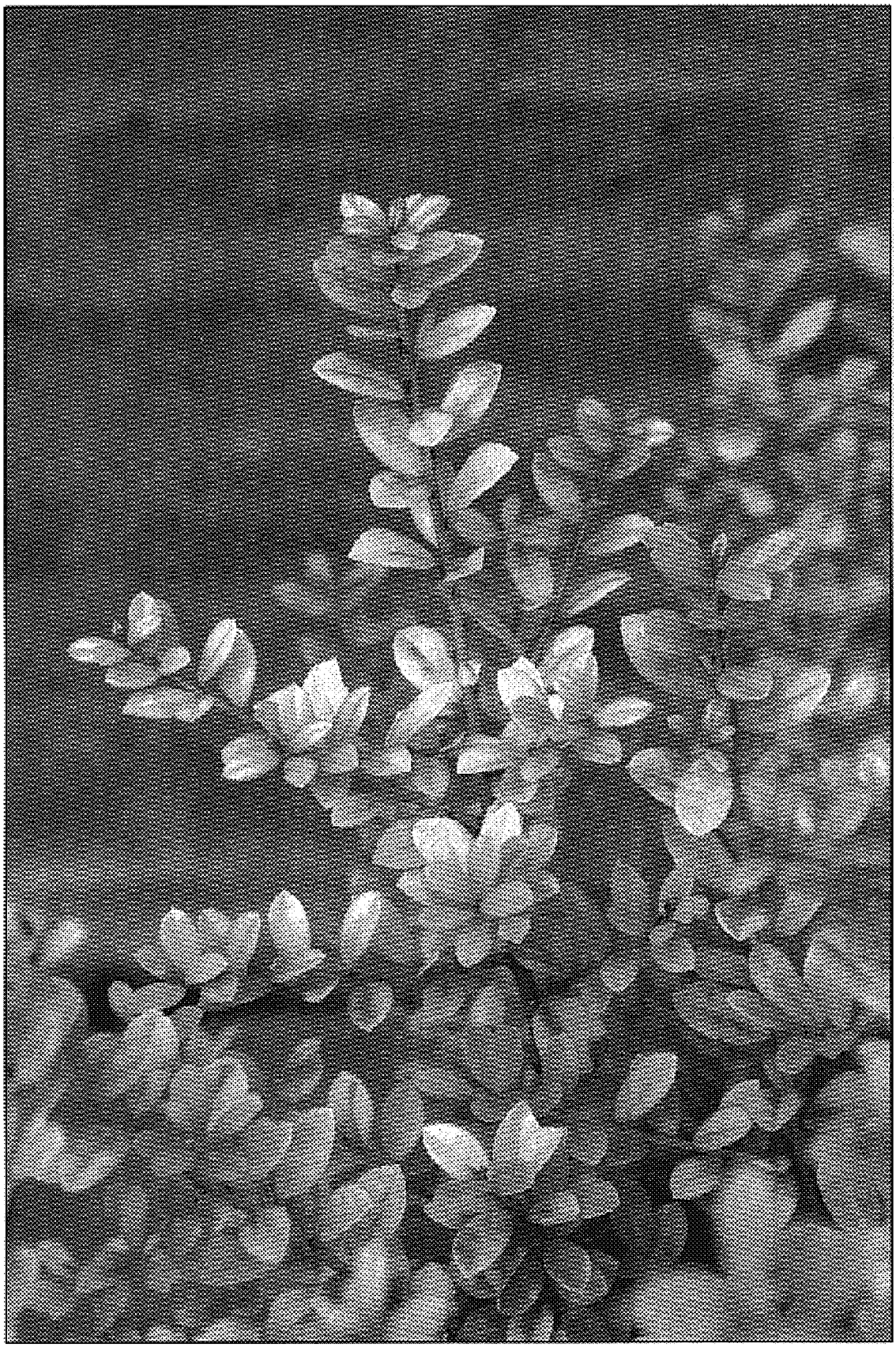

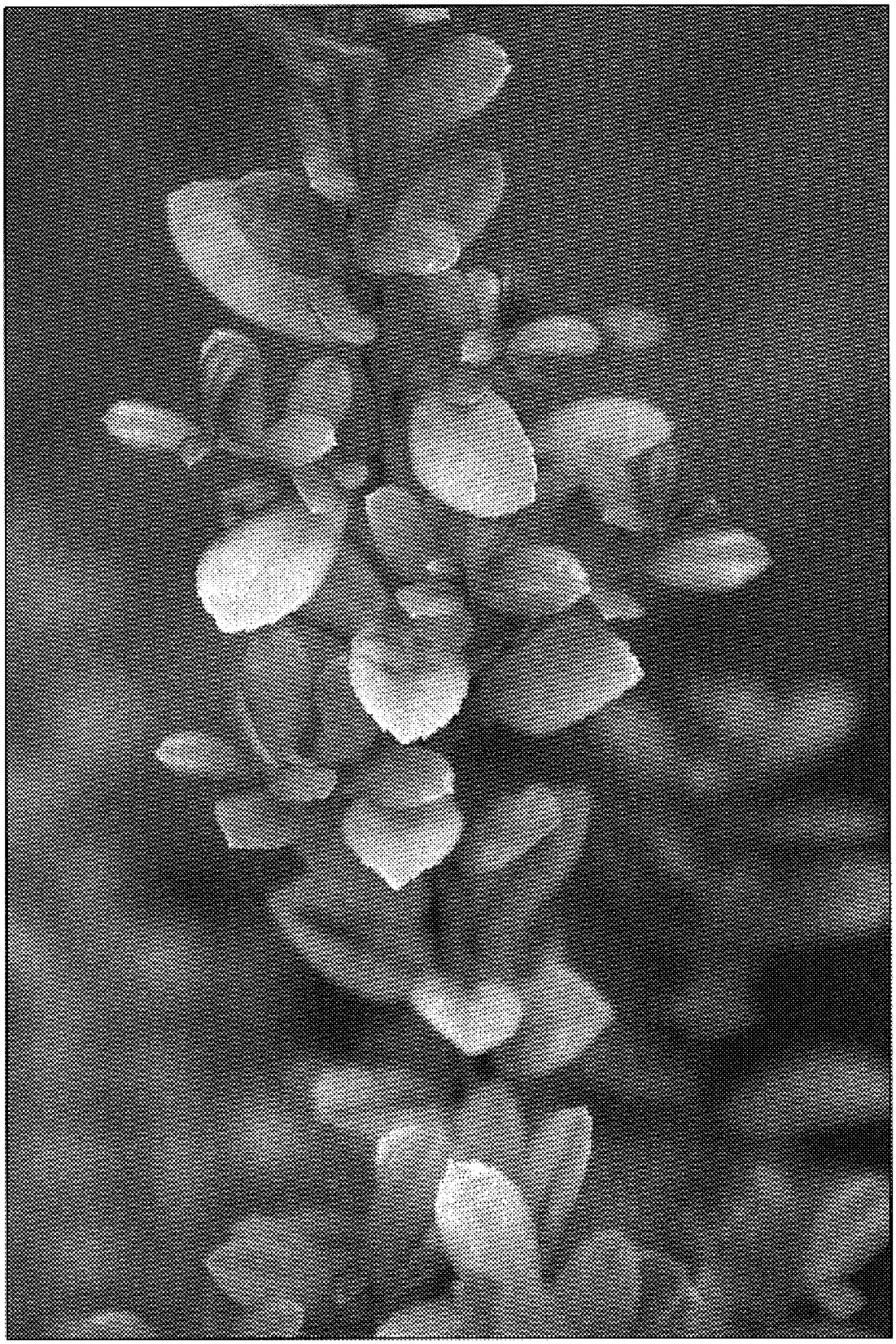

* * * * *